USU09353074B2

(12) United States Patent
Coupard et al.

(10) Patent No.: US 9,353,074 B2
(45) Date of Patent: *May 31, 2016

(54) THERMALLY INTEGRATED PROCESS FOR THE PRODUCTION OF ETHYLENE OXIDE FROM A FLOW OF ETHANOL

(71) Applicant: IFP Energies nouvelles, Rueil-Malmaison Cedex (FR)

(72) Inventors: Vincent Coupard, Villeurbanne (FR); Thomas Plennevaux, Lyons (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/767,184

(22) PCT Filed: Feb. 6, 2014

(86) PCT No.: PCT/FR2014/050227
§ 371 (c)(1),
(2) Date: Aug. 11, 2015

(87) PCT Pub. No.: WO2014/125192
PCT Pub. Date: Aug. 21, 2014

(65) Prior Publication Data
US 2015/0376151 A1 Dec. 31, 2015

(30) Foreign Application Priority Data
Feb. 12, 2013 (FR) ........................... 1351163

(51) Int. Cl.
*C07D 301/03* (2006.01)
*C07D 303/04* (2006.01)
*C07C 1/24* (2006.01)

(52) U.S. Cl.
CPC ............. *C07D 301/03* (2013.01); *C07C 1/24* (2013.01); *C07D 303/04* (2013.01)

(58) Field of Classification Search
CPC ........ C07D 301/03; C07D 303/04; C07C 1/24
USPC ........................................................ 549/523
See application file for complete search history.

(56) References Cited

U.S. PATENT DOCUMENTS

| 3,119,837 | A | 1/1964 | Kinglsey et al. |
| 4,396,789 | A | 8/1983 | Barrocas et al. |

FOREIGN PATENT DOCUMENTS

WO 2007/134415 A2 11/2007

OTHER PUBLICATIONS

International Search Report dated Apr. 2, 2014 issued in corresponding PCT/FR2014/050227 application (pp. 1-3).
M. Bruscino "Scientific Design's Ethanol to Monoethylene Glycol Technology", Hidrocarbon World, vol. 5, No. 2 (Jan. 1, 2010) pp. 12, 14-16.

*Primary Examiner* — T. Victor Oh
(74) *Attorney, Agent, or Firm* — Millen White Zelano and Branigan, PC; John Sopp; Anthony Zelano

(57) ABSTRACT

Process for dehydrating an ethanol feed to ethylene then oxidating the ethanol to ethylene oxide, comprising vaporizing the feed and a flow of diluting water comprising recycled ethanol to produce a vaporized feed, dehydrating a mixture of vaporized feed and a vaporized flow of diluting water comprising ethanol, separating the dehydration effluent into ethylene and water effluents, purifying at least a portion of the water effluent and separating a flow of treated water and a flow of diluting water comprising ethanol, recycling and vaporizing at least a portion of the separated diluting water by partial or complete vaporization in an exchanger using heat exchange with a quench flow obtained from the oxidation, said quench flow, cooled, then recycled to the oxidation reactor(s), and oxidation of the ethylene in the effluent comprising ethylene into ethylene oxide, this oxidation using a tubular oxidation reactor cooled by vaporization of said quench flow.

13 Claims, 1 Drawing Sheet

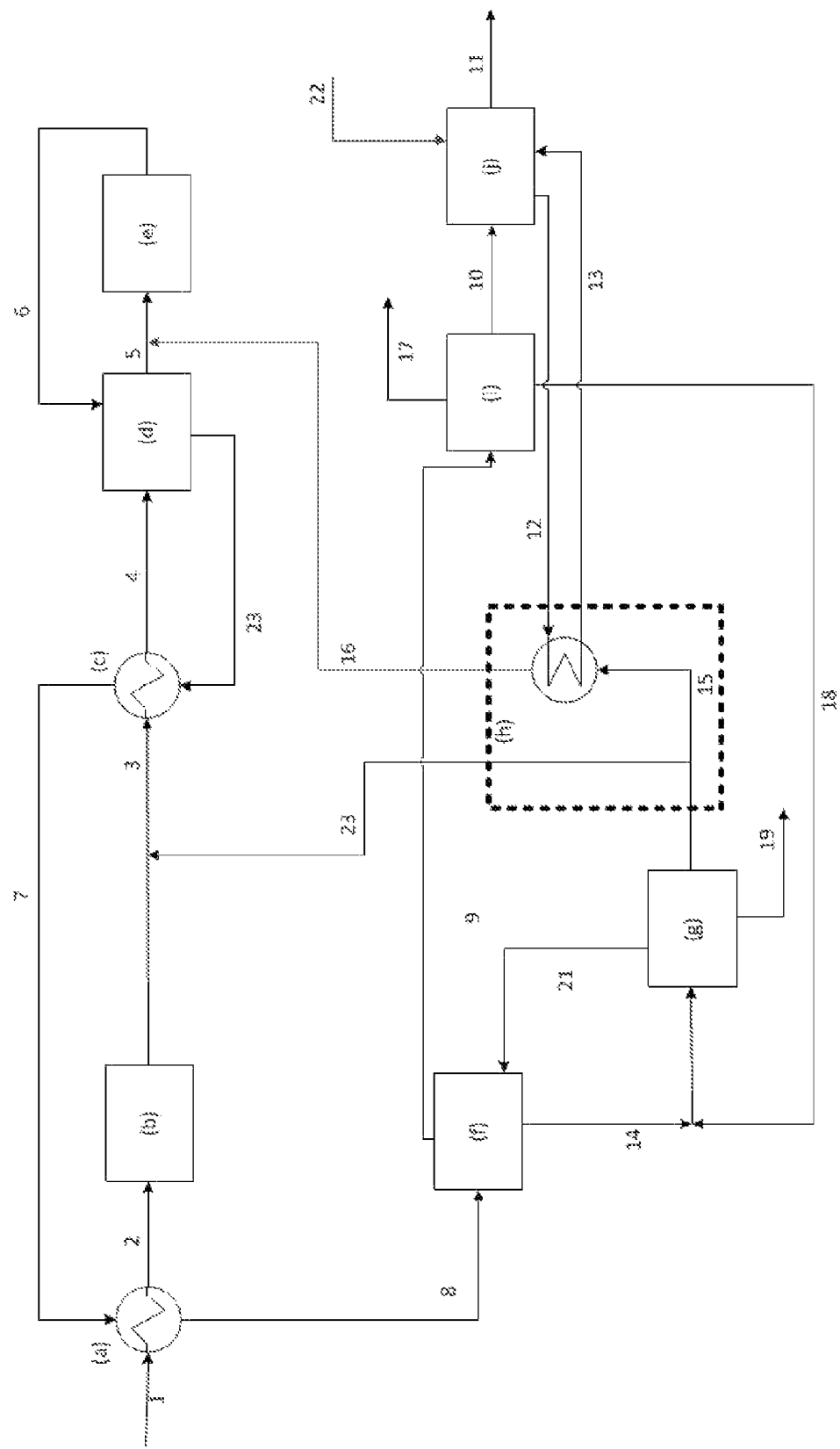

THERMALLY INTEGRATED PROCESS FOR THE PRODUCTION OF ETHYLENE OXIDE FROM A FLOW OF ETHANOL

FIELD OF THE INVENTION

The present invention relates to a process for the transformation of ethanol to ethylene oxide including a thermally integrated step for dehydration of ethanol and a thermally integrated step for oxidation of the ethylene produced.

PRIOR ART

The ethanol to ethylene dehydration reaction has been known in detail since the end of the 19$^{th}$ century. "The Dehydration of Alcohols over Alumina. I: The reaction scheme", H. Knözinger, R. Köhne, Journal of Catalysis (1966), 5, 264-270 is considered to be the baseline publication regarding studies of alcohol dehydration, including that of ethanol. This reaction is known to be highly endothermic, equilibrated and displaced towards ethanol at high temperatures. The drop in temperature corresponding to the total conversion of pure ethanol in an adiabatic reactor is 380° C. At lower temperatures, the ethanol is converted into diethyl ether (DEE). This reaction "intermediate" may be present in ethylene dehydration reactions in which the conversion is partial, or between two reactors in multi-reactor processes. DEE may then be converted into ethylene at a higher temperature. The reference catalyst which is frequently used is a monofunctional acid catalyst; gamma alumina is the most cited catalyst. Zeolites are also used for this application, in particular ZSM-5 since the 1980s—see, for example, "Reactions of ethanol over ZSM-5", S. N. Chaudhuri & al., Journal of Molecular Catalysis 62:289-295 (1990).

U.S. Pat. No. 4,232,179 describes a process for the dehydration of ethanol to ethylene in which the heat necessary for the reaction is supplied by introducing a heat transfer fluid mixed into the reactor with the feed. The heat transfer fluid is either steam from an external source or an external flow originating in the process, or a recycle of a portion of the effluent from the dehydration reactor, i.e. ethylene which is produced. Introducing a mixture of the feed with said heat transfer fluid means that the heat necessary to maintain the temperature of the catalytic bed at a level compatible with the desired conversions can be provided. In the case in which the heat transfer fluid is the effluent from the dehydration reactor, a compressor for recycling said effluent is necessary. However, recycling the ethylene produced by the reaction constitutes a disadvantage, as the introduction of ethylene modifies the equilibrium of the dehydration reaction. In addition, ethylene participates in secondary oligomerization reactions, hydrogen transfer reactions and olefin disproportionation reactions; these are reactions with an order of more than 0 with respect to their reagent. Increasing the concentration of ethylene right from the start of the reaction multiplies the formation of by-products. The loss of ethylene is thus higher, which results in a drop in selectivity.

Patent application WO 2007/134415 describes a process for the dehydration of ethanol to ethylene which has been improved compared with U.S. Pat. No. 4,232,179 in order to reduce the investment costs due to a reduced amount of equipment and reduced operational costs because steam external to the process is not used. In that process, at least a portion of the effluent from the dehydration reactor (mixture of the ethylene produced and steam) and superheated steam obtained from the water produced by dehydration of the ethanol and condensed in the reactor are used as the heat transfer fluid and enter the dehydration reactor as a mixture with the ethanol. Said patent application is silent as to the pressure conditions to be applied between the ethanol feed and the effluent with the aim of maximizing heat exchange.

U.S. Pat. No. 4,396,789 also describes a process for the dehydration of ethanol to ethylene, in which the ethanol and steam acting as a heat transfer fluid are introduced into the first reactor at a temperature in the range 400° C. to 520° C. and at a high pressure in the range 20 to 40 atm, such that the effluent produced by the dehydration reaction is withdrawn from the last reactor at a pressure of no less than 18 atm, said reaction product, i.e. ethylene, being capable of undergoing the final cryogenic distillation step after cooling without an intermediate compression step. Said process is also characterized by an exchange of heat between said dehydration reaction product and the feed introduced into the first reactor, said reaction product being used to vaporize the feed entering the first reactor. The unconverted ethanol, at least a portion of the water formed during the reactions of the process and the water added for the final wash of the gases are recycled to ensure complete conversion of the ethanol.

Patent application WO 2011/002699 discloses a process for the dehydration of an ethanol feed to ethylene, comprising vaporization of a mixture of ethanol and water and reaction of this mixture in an adiabatic reactor. That application does not address the problem of maximizing the recovery of heat with a view to reducing the energy consumption of the process.

U.S. Pat. No. 3,119,837 describes a process for the oxidation of ethylene in the presence of a catalyst based on silver. It is based on the positive effect of methane on the selectivity of the reaction for the conversion of ethylene to ethylene oxide and gives the operating conditions for oxidation in the presence of purified oxygen. The principal operating conditions that are given are as follows: temperature in the range 200° C. to 300° C. (preferably) and pressure in the range 15 to 500 psi absolute (preferably).

Patent EP 0 496 470 B1 describes an oxidation catalyst which may be used in the process described in U.S. Pat. No. 3,119,837. That patent describes the principal characteristics of the catalyst as well as the operating condition ranges (temperatures) in which it can be used. The catalyst described is based on silver and the operating conditions are compatible with those described in U.S. Pat. No. 3,119,837.

Mike Bruscino, "Scientific Design's Ethanol to Monoethylene Glycol Technology", Hydrocarbon World, Vol. 5(2), pp. 15-17 (2010) describes a process for the production of ethylene glycol from an ethanol bioresource including a process for the dehydration of ethanol to ethylene, a process for oxidation of the ethylene produced thereby and a process for the conversion of ethylene oxide to glycol. The process described does not consider recycling water to the dehydration section, nor does it consider thermal integration between the oxidation section and the dehydration section.

One aim of the invention is to provide a process for the production of ethylene oxide, comprising a step for dehydration of ethanol to ethylene and a step for catalytic oxidation of the ethylene produced, these two steps being integrated with each other in order to reduce the energy consumption and the water consumption, said reductions being effected by a particular arrangement of the thermal integration and the use of appropriate operating conditions, in particular matching of the evacuation of the heat generated by the oxidation reaction and the level of dilution necessary at the inlet to the dehydration step.

SUMMARY AND ADVANTAGE OF THE INVENTION

The invention describes a process for the production of ethylene oxide from ethanol. This process consists of the integration of two distinct processes: catalytic dehydration of the ethanol, and oxidation of the ethylene produced.

The process for the dehydration of an ethanol feed to form ethylene preferably comprises a step for pre-treatment which reduces the quantity of organic or basic nitrogen contained in said feed and converts a fraction of the ethanol to DEE, and a step for vaporization of the pre-treated ethanol feed mixed with at least a portion of a flow of diluting water comprising ethanol, in an exchanger by means of an exchange of heat with the effluent obtained from the last dehydration reactor. The catalytic oxidation process employs at least one multi-tube reactor cooled by vaporization of a heat transfer fluid, said fluid preferably comprising water, in the shell of the reactor.

Said invention has the advantage over prior art processes of reducing the consumption of water and of reducing the energy consumption necessary for conversion of the ethanol to ethylene oxide.

The ethylene oxide produced is a reaction intermediate in the synthesis of many products, for example glycols, polyols, ethoxylates, glycol ethers or ethanolamines.

DESCRIPTION OF THE INVENTION

The invention concerns a process for the dehydration of an ethanol feed to ethylene then oxidation of the ethylene to ethylene oxide, comprising:

a) an optional step for preheating said ethanol feed to a temperature in the range 70° C. to 130° C. by heat exchange with the effluent obtained from step e);

b) an optional step for pre-treatment of the ethanol feed over an acidic solid operating at a temperature in the range 70° C. to 130° C. in order to produce a pre-treated ethanol feed;

c) a step for vaporization of a vaporization feed comprising said pre-treated ethanol feed and at least a portion of the flow of diluting water comprising ethanol recycled in accordance with step h) to an exchanger by means of an exchange of heat with the effluent obtained from the last reactor of step e), said vaporization feed being introduced into said vaporization step at a pressure in the range 0.1 to 1.4 MPa so as to produce a vaporized feed;

d) a step for compressing and superheating said vaporized feed in a compressor so as to produce a feed which is compressed and at the temperature for supplying to the dehydration section e);

e) a step for dehydration of a mixture comprising said compressed feed and the vaporized flow of diluting water comprising the ethanol obtained from step h), said mixture having a ratio of water to ethanol in the range 1 to 4 by weight, in at least one adiabatic reactor containing at least one dehydration catalyst and in which the dehydration reaction takes place, operating at an inlet temperature in the range 350° C. to 550° C. and at an inlet pressure in the range 0.3 to 1.8 MPa;

f) a step for separating the effluent obtained from the last adiabatic reactor of step e) into an effluent comprising ethylene at a pressure of less than 1.6 MPa and an effluent comprising water;

g) a step for purification of at least a portion of the effluent comprising water obtained from step f) and separation into at least a flow of treated water and a flow of diluting water comprising ethanol;

h) a step for recycling and vaporization of at least a portion of the flow of diluting water comprising ethanol obtained from step g) by partial or total vaporization in an exchanger using heat exchange with a quench flow obtained from oxidation step j) in a vaporization exchanger, said quench flow, cooled, then being recycled to the reactor or reactors of oxidation step j), said flow of at least partially vaporized diluting water comprising ethanol being recycled upstream of step e), the non-vaporized portion of the flow of treated water obtained from step g) being recycled to the inlet to vaporization step c);

i) a step for compression and, preferably, for purification of the effluent comprising ethylene obtained from step f);

j) a step for oxidation of the ethylene comprised in the effluent comprising ethylene obtained from step i) into ethylene oxide, this oxidation step comprising at least one tubular oxidation reactor cooled by vaporization of said quench flow preferably comprising water obtained from step h), said quench flow which has thus been reheated being recycled to step h).

Feed

In accordance with the invention, the feed treated in the process is an ethanol feed.

Said ethanol feed is advantageously a concentrated ethanol feed. The term "concentrated ethanol feed" means an ethanol feed comprising a percentage by weight of ethanol of 35% by weight or more. Preferably, said concentrated ethanol feed comprises a percentage by weight of ethanol in the range 35% to 99.9% by weight.

The ethanol feed comprising less than 35% by weight of ethanol may be concentrated using any means known to the skilled person, for example by distillation, absorption or pervaporation.

In addition to water, said ethanol feed also advantageously comprises a quantity of alcohols other than ethanol, such as methanol, butanol and/or isopentanol for example, of less than 10% by weight, preferably less than 5% by weight, a quantity of oxygen-containing compounds other than alcohols such as ethers, acids, ketones, aldehydes and/or esters, of less than 1% by weight and a quantity of nitrogen and sulphur, organic and mineral, of less than 0.5% by weight, the percentages by weight being expressed with respect to the total weight of said feed.

The ethanol feed treated in the process of the invention is optionally obtained by a process for the synthesis of alcohol from fossil fuels such as from coal, natural gas or carbonaceous waste, for example.

Said feed may also advantageously derive from non-fossil sources. Preferably, the ethanol feed treated in the process of the invention is an ethanol feed produced from renewable source material obtained from biomass, often known as "bioethanol". Bioethanol is a feed produced by a biological pathway, preferably by fermentation of sugars obtained, for example, from cultures of sugar-containing plants such as sugar cane (saccharose, glucose, fructose and sucrose), beet, or from amylaceous plants (starch) or from lignocellulosic biomass or from hydrolysed cellulose (mainly glucose and xylose, galactose), containing variable quantities of water.

For a more complete description of conventional fermenting processes, reference may be made to the publication "Les Biocarburants, Etat des lieux, perspectives et enjeux du developpement [Biofuels—state of play, perspectives and challenges for development], Daniel Ballerini, Editions Technip".

Said feed may also advantageously be obtained from synthesis gas.

Said feed may also advantageously also be obtained by hydrogenation of the corresponding acids or esters. In this case, acetic acid or acetic esters are advantageously hydrogenated to ethanol using hydrogen. Acetic acid may advantageously be obtained by carbonylation of methanol or by fermentation of carbohydrates.

Preferably, the ethanol feed treated in the process of the invention is an ethanol feed produced from renewable sources obtained from biomass.

Preheating Step a)

The ethanol feed optionally undergoes a step a) for preheating in a heat exchanger so as to produce a preheated ethanol feed by means of an exchange of heat with the effluent obtained from dehydration step e). When a pre-treatment step b) is carried out, the temperature at the end of step a) is in the range 70° C. to 130° C., preferably in the range 110° C. to 130° C. The pressure of the ethanol feed is adjusted so that it remains liquid at the end of preheating step a), at a value in the range 0.1 to 3 MPa.

Pre-Treatment Step b)

The ethanol feed, optionally preheated, optionally undergoes a step b) for pre-treatment so as to produce a pre-treated ethanol feed. Said pre-treatment step can be used to eliminate the nitrogen-containing compounds present in said preheated feed so as to limit deactivation of the dehydration catalyst placed downstream.

Said pre-treatment step b) is carried out over an acidic solid, preferably an acidic resin, and at a temperature in the range 70° C. to 130° C., preferably in the range 110° C. to 130° C.

Said pre-treatment step b) can be used to eliminate impurities, basic and/or organic, and cationic species in order to obtain a pre-treated ethanol feed the level of impurities of which is compatible with the dehydration catalyst.

Pre-treatment over the acidic solid under the operating conditions of the invention means that between 3% by weight and 20% by weight, preferably between 8% and 12% by weight of the ethanol present in said feed can be converted into DEE, the percentage by weight being determined with respect to the total weight of ethanol present in said feed at the inlet to pre-treatment step b).

The acidic solid includes all of the acidic solids known to the skilled person: silica-aluminas, acid clays, zeolites, sulphated zirconias, acidic resins, etc. The essential fact is that the acidic solid has a high exchange capacity in order to capture as many of the basic and cationic species as possible, and a sufficiently high acid strength to carry out the partial transformation of ethanol to DEE.

Acidic solids which are readily commercially available are clays treated with acids to make them acidic (such as montmorillonite) and zeolites with a silica to alumina ratio in the crystalline lattice of 2.5 to 100 molar.

The acidic resin includes sulphonic groups grafted onto an organic support composed of aromatic and/or haloaliphatic chains. Preferably, the acidic solids have an exchange capacity of at least 0.1 mmol $H^+$ equivalent per gram.

The acidic resin is prepared by polymerization or copolymerization of aromatic vinyl groups followed by a sulphonation, said aromatic vinyl groups being selected from styrene, vinyl toluene, vinyl naphthalene, vinyl ethyl benzene, methyl styrene, vinyl chlorobenzene and vinyl xylene, said resin having a degree of cross-linking in the range 20% to 35%, preferably in the range 25% to 35% and preferably equal to 30%, and an acid strength, measured by potentiometry during neutralization with a KOH solution, of 0.2 to 10 mmol $H^+$ equivalent per gram, and preferably 0.2 to 2.5 mmol $H^+$ equivalent per gram.

Said acidic ion exchange resin contains between 1 and 2 terminal sulphonic groups per aromatic group. It is in the range 0.15 to 1.5 mm in size. The term "resin size" means the diameter of the smallest sphere encompassing the particle of resin. Resin size classes are measured by sieving on suitable sieves using a technique which is known to the skilled person.

A preferred resin is a resin constituted by copolymers of monovinyl aromatics and polyvinyl aromatics, highly preferably a copolymer of divinylbenzene and polystyrene with a degree of cross-linking in the range 20% to 45%, preferably in the range 30% to 40%, and more preferably equal to 35% and with an acid strength, representing the number of active sites of said resin, measured by potentiometry during neutralization with a KOH solution, in the range 1 to 10 mmol $H^+$ equivalent per gram, and preferably in the range 3.5 to 6 mmol $H^+$ equivalent per gram. As an example, the resin is a TA801 resin sold by Axens.

The acidic solids may be regenerated from time to time once the exchange capacity has been almost completely saturated by adsorption of basic and cationic species in situ or ex situ. In the case of inorganic acidic solids such as clays and zeolites, regeneration may consist of simply heating at high temperature in order to desorb the basic species in the presence of an inert flow or a flow containing oxygen. The cations may be removed by ion exchange. The acidic resins may be regenerated by ion exchange, typically by a treatment with an acid in the liquid phase. The acidic solids may also be used once until saturation and replaced with fresh solid.

The acidic solid may be used alone or as a mixture with other types of acidic solids. Mixtures of different acidic solids or sequences of acidic solids may be used in order to optimize the adsorption capacity of the basic and cationic species and the capacity for partially transforming ethanol to DEE.

The pre-treatment described above may advantageously be supplemented by a pre-treatment using an anion exchange resin. This resin may, for example, be a resin charged with sodium, or trimethylammonium characterized by an exchange capacity measured in mg ($OH^-$/liter). This resin may be Amberlite IRN78 resin, for example. This supplemental resin can be used to retain sulphate ions, $SO_4^{2-}$, in order to extend the life of the catalyst.

Vaporization Step c)

The mixture comprising said pre-treated ethanol feed and at least a portion of the flow of diluting water comprising ethanol recycled in accordance with recycling and vaporization step h) is known as the "vaporization feed".

In accordance with the invention, the dehydration process comprises a step c) for vaporization of said vaporization feed so as to produce a vaporized feed. Said vaporization is carried out by means of an exchange of heat with the effluent obtained from dehydration step e) in a heat exchanger.

Preferably, said vaporization feed is introduced into said vaporization step c) at a pressure which is lower than the pressure of the effluent obtained from dehydration step e).

The pressure of said vaporization feed upstream of vaporization step c) is advantageously selected such that the temperature difference in the heat exchanger between the effluent obtained from the dehydration step e) which is condensed and said vaporization feed which is evaporated is no less than 2° C., preferably no less than 3° C.

This difference in temperature in the heat exchanger is known as the approach to thermal equilibrium.

Adjustment of said pressure upstream of the vaporization step c) is an essential criterion of the present invention. This pressure is selected so as to be as high as possible, so that the difference between the condensation temperature of the effluent from dehydration step e) and the vaporization temperature of said vaporization feed is 2° C. or more, preferably 3° C. or more, in order to maximize the exchange of heat between said vaporization feed and said effluent obtained from the dehydration step e).

In a preferred arrangement in which the pre-treatment step b) is carried out, the vaporization temperature of the vaporization feed at a given pressure is reduced compared with that of a feed obtained by a concatenation which does not include the pre-treatment step b). For a given condensation temperature of the effluent from the dehydration step e) and a fixed approach to thermal equilibrium, then, the pressure upstream of the vaporization step c) may be adjusted to a higher value than that which would have existed in a concatenation not including the pre-treatment step b).

Adjustment of said pressure upstream of the vaporization step c) to the highest value possible, within the limits determined in the preceding paragraph, means that the energy necessary for compression during the compression step d) of the process of the invention can be minimized.

Said vaporization feed is introduced into said vaporization step c) at a pressure in the range 0.1 to 1.4 MPa, preferably in the range 0.2 to 0.6 MPa.

Introducing said vaporization feed into the vaporization step c) at this specific pressure in the range 0.1 to 1.4 MPa, preferably in the range 0.2 to 0.6 MPa, below the pressure of the effluent leaving the final reactor of the dehydration step e), means that a vaporization temperature for said vaporization feed below the condensation temperature of the effluent obtained from the last adiabatic reactor can be exploited. Thus, the major portion of the latent heat of the aqueous phase of the effluent obtained from the last adiabatic reactor is recovered in order to vaporize said vaporization feed without adding external heat. The whole of the enthalpy of vaporization of said vaporization feed is thus exchanged with the enthalpy of condensation of said effluent.

Compression and Superheating Step d)

In accordance with the invention, said vaporized feed undergoes a compression in a compression step d) so as to produce a compressed feed. Said compression step d) is advantageously carried out in any type of compressor known to the skilled person. In particular, compression step d) is advantageously carried out in a compressor of the integrally geared centrifugal compressor type or in a compressor comprising one or more blowers with a radial wheel in series without intermediate cooling, or in a volumetric type compressor with or without lubrification.

In an arrangement in which step b) is carried out, said step b) can surprisingly be carried out at a higher pressure upstream of step c); the degree of compression in step d) is reduced in order to obtain a given pressure at the outlet from said step d), thereby reducing the energy consumption of said step d).

The compression step d) can be used to produce a heat pump which is integrated into said process, using the flows obtained from the process and not involving an external heat transfer fluid.

The combination of the specific operating conditions of step c) and step d) means that the addition of external heat transfer fluid to the process to ensure vaporization of said vaporization feed can be avoided by recovering the major portion of the latent heat of the aqueous phase of the effluent obtained from the last adiabatic reactor in order to vaporize the vaporization feed. Thus, only flows obtained from the process are used.

The pressure of said compressed feed obtained from compression step d) is advantageously in the range 0.3 to 1.8 MPa, preferably in the range 0.5 to 1.3 MPa. The pressure at the outlet for said feed is sufficiently high for the condensation temperature of the effluent obtained from the last reactor to be higher than the vaporization temperature for the feed entering step c), which is a necessary condition for step c) to be feasible.

Said compressed feed obtained from the compression step d) is optionally heated in a single phase type gas exchanger by means of an exchange of heat with the effluent obtained from the last adiabatic reactor of step e). In said single phase type gas exchanger, said compressed feed is superheated and the effluent obtained, in the gaseous state, from the last adiabatic reactor of step e) is "desuperheated" without being condensed.

Said compressed feed is advantageously superheated to an outlet temperature in the range 250° C. to 420° C., preferably in the range 280° C. to 410° C. At the outlet from said single phase type gas exchanger of the last adiabatic reactor of step e), the effluent obtained, in the gaseous state, is advantageously at a temperature in the range 180° C. to 260° C.

Thus, using the various exchangers of the single phase gas and gas/liquid evaporator type, and vaporization at a pressure below the pressure of the effluent leaving the last reactor of said vaporization feed means that condensation of at least 60% of the water vapour present in the effluent obtained from the last reactor of the dehydration step e) can be carried out.

The single phase type gas exchanger is an exchanger the technology of which is known to the skilled person, which can be used to minimize pressure drops while providing a large exchange surface. This low pressure gas/gas exchange induces a low heat flux density through the wall of the exchanger (low transfer coefficient), which necessitates having a large exchange surface. In addition, the loss of pressure has to be minimized in order to limit the load on the compressor of step d). As an example, this exchanger may be a pressurized plate exchanger in a shell, of the Packinox type provided by Alpha Laval.

Dehydration Step e)

In accordance with the invention, said compressed feed, optionally heated, is mixed with the vaporized flow of diluting water comprising ethanol obtained from step h) for recycling and vaporization. The mixture is advantageously introduced into a furnace so as to bring it to an inlet temperature in at least one adiabatic reactor which is compatible with the dehydration reaction temperature. It then undergoes a dehydration step e) in at least one adiabatic reactor containing at least one fixed bed of dehydration catalyst and in which the dehydration reaction takes place.

The mixture at the inlet to step e) for dehydration of the flow constituted by the ethanol feed and the flow of diluting water comprising ethanol obtained from step g) is produced in a manner such that at the end of mixing, the weight ratio of water to ethanol, known as the dilution ratio, is in the range 1 to 4. Dilution is intended to reduce the partial pressures of ethanol in the reactor or reactors and to render the process more selective for ethylene. This weight ratio is adjusted by modifying the flow rate of treated water at the end of step g) and/or by modifying the flow rate of the ethanol feed.

The dehydration step e) is advantageously carried out in one or two reactors.

In the case in which step e) is carried out in an adiabatic reactor, said compressed feed, optionally heated, is advantageously introduced into said reactor at an inlet temperature in the range 350° C. to 550° C., preferably in the range 400° C. to 500° C., and at an inlet pressure in the range 0.3 to 1.8 MPa, preferably in the range 0.4 to 0.8 MPa.

The effluent obtained from said adiabatic reactor of step e) is advantageously at a temperature in the range 270° C. to 450° C., preferably in the range 340° C. to 430° C., and with an outlet pressure in the range 0.2 to 1.6 MPa, preferably in the range 0.3 to 0.8 MPa.

In the case in which step e) is carried out in two adiabatic reactors, said compressed feed, also optionally heated, is advantageously introduced into the first reactor at an inlet temperature in the range 350° C. to 550° C., preferably in the range 370° C. to 500° C., and at an inlet pressure in the range 0.3 to 1.8 MPa, preferably in the range 0.4 to 1.1 MPa.

The effluent obtained from the first adiabatic reactor advantageously leaves said first reactor at a temperature in the range 270° C. to 450° C., preferably in the range 290° C. to 390° C., and at a pressure in the range 0.3 to 1.7 MPa, preferably in the range 0.3 to 1.0 MPa.

Said effluent is advantageously introduced into a furnace in a manner such that the inlet temperature for said effluent into the second adiabatic reactor is in the range 350° C. to 550° C., preferably in the range 400° C. to 500° C. Said effluent has an inlet pressure into said second reactor which is advantageously in the range 0.3 to 1.7 MPa, preferably in the range 0.3 to 0.9 MPa.

The effluent obtained from the second adiabatic reactor leaves said second adiabatic reactor at a temperature which is advantageously in the range 270° C. to 450° C., preferably in the range 340° C. to 430° C. The outlet pressure for said effluent obtained from the second adiabatic reactor is advantageously in the range 0.2 to 1.6 MPa, preferably in the range 0.3 to 0.8 MPa.

The inlet temperature for the reactor or reactors may advantageously be gradually increased in order to prevent deactivation of the dehydration catalyst.

The dehydration reaction which takes place in at least one adiabatic reactor of step e) of the process of the invention advantageously operates at a weight hourly space velocity in the range 0.1 to 20 $h^{-1}$, preferably in the range 0.5 to 15 $h^{-1}$. The weight hourly space velocity is defined as the ratio of the mass flow rate of the pure ethanol feed over the weight of catalyst.

The dehydration catalyst used in step e) is a catalyst which is known to the skilled person. Said catalyst is preferably an amorphous acid catalyst or a zeolitic acid catalyst.

In the case in which the dehydration catalyst used in step e) is a zeolitic catalyst, said catalyst comprises at least one zeolite selected from zeolites having at least pore openings containing 8, 10 or 12 oxygen atoms (8 MR, 10 MR or 12 MR). It is in fact known to define the pore size of zeolites by the number of oxygen atoms forming the annular section of the channels of the zeolites, known as the "member ring" or MR. Preferably, said zeolitic dehydration catalyst comprises at least one zeolite with a structure type selected from structure types MFI, FAU, MOR, FER, SAPO, TON, CHA, EUO and BEA. Preferably, said zeolitic dehydration catalyst comprises a zeolite with structure type MFI, and more preferably a ZSM-5 zeolite.

The zeolite employed in the dehydration catalyst used in step e) of the process of the invention may advantageously be modified by dealumination or desilication using any dealumination or desilication method known to the skilled person.

The zeolite employed in the dehydration catalyst used in step e) of the process of the invention or the final catalyst may advantageously be modified by an agent of a nature such as to attenuate its total acidity and to improve its hydrothermal resistance properties. Preferably, said zeolite or said catalyst advantageously comprises phosphorus, preferably added in the form of $H_3PO_4$, followed by steam treatment after neutralization of the excess acid with a basic precursor such as calcium, Ca, for example. Preferably, said zeolite has a phosphorus content in the range 1% to 4.5% by weight, preferably in the range 1.5% to 3.1% by weight with respect to the total catalyst weight.

Preferably, the dehydration catalyst used in step e) of the process of the invention is the catalyst described in patent applications WO/2009/098262, WO/2009/098267, WO/2009/098268, or WO/2009/098269.

In the case in which the dehydration catalyst used in step e) is an amorphous acid catalyst, said catalyst comprises at least one porous refractory oxide selected from alumina, alumina activated by a deposit of mineral acid, and silica-alumina.

Said amorphous or zeolitic dehydration catalyst used in step e) of the process of the invention may advantageously also comprise at least one oxide type matrix also known as a binder. The term "matrix of the invention" means an amorphous or crystalline matrix or a matrix comprising amorphous and crystalline portions. Said matrix is advantageously selected from elements of the group formed by clays (such as natural clays, for example kaolin or bentonite), magnesia, aluminas, silicas, silica-aluminas, aluminates, titanium oxide, boron oxide, zirconia, aluminium phosphates, titanium phosphates, zirconium phosphates and charcoal, used alone or as a mixture. Preferably, said matrix is selected from elements from the group formed by aluminas, silicas and clays.

Said dehydration catalyst used in step e) of the process of the invention is advantageously shaped into the form of grains with various shapes and dimensions. It is advantageously used in the form of cylindrical or polylobed extrudates such as bilobes, trilobes, polylobes in a straight or twisted form, but may optionally be fabricated and employed in the form of a crushed powder, tablets, rings, beads, wheels or spheres. Preferably, said catalyst is in the form of extrudates.

Said dehydration catalyst used in step e) of the process of the invention is advantageously deployed in at least one reactor, in a fixed bed or moving bed.

In step e) of the process of the invention, the catalysts used and the operating conditions are selected so as to maximize the production of ethylene. The overall dehydration reactions involved in step e) of the process of the invention are as follows:

$$2C_2H_5OH \rightarrow 2CH_2=CH_2+2H_2O$$

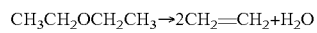

$$CH_3CH_2OCH_2CH_3 \rightarrow 2CH_2=CH_2+H_2O$$

Conversion of the ethanol feed in step e) is more than 90%, preferably 95% and more preferably more than 99%.

A conversion of less than 90% has the effect of dropping the overall yield of the process, as a large quantity of DEE which is not converted into ethylene is lost in the downstream separation steps.

Conversion of the ethanol feed is defined, as a percentage, by the following formula:

[1−(hourly mass of ethanol at outlet/hourly mass of ethanol at inlet)]×100

The hourly mass of ethanol at the inlet and outlet is measured in a conventional manner, for example by chromatography.

Step e) in which the dehydration reaction takes place is advantageously carried out in one or two reactors. A preferred reactor is a radial reactor functioning in upflow mode or downflow mode. During step e) of the process of the invention, transformation of the feed is accompanied by deactivation of the dehydration catalyst by coking and/or by adsorption of inhibiting compounds. Thus, the dehydration catalyst periodically has to undergo a regeneration step. Preferably, the reactor is used in an alternating regeneration mode reactor, also known as a swing reactor, in order to alternate reaction phases with phases for regeneration of said dehydration catalyst. The aim of this regeneration treatment is to burn off the organic deposits along with the species containing nitrogen and sulphur contained at the surface and within said dehydration catalyst. The pre-treatment step b) carried out in this invention can be used to reduce the quantity of impurities, basic and organic, as well as the cationic species which would alter the cycle time of the catalyst. Eliminating these species thus means that the number of catalyst regenerations can be limited.

Regeneration of the dehydration catalyst used in said step e) is advantageously carried out by oxidation of coke and inhibiting compounds in a flow of air or in an air/nitrogen mixture, for example employing recirculation of the combustion air with or without water in order to dilute the oxygen and control the exothermic nature of the regeneration. In this case, the oxygen content at the inlet to the reactor can advantageously be adjusted by adding air. Regeneration takes place at a pressure in the range between atmospheric pressure and the reaction pressure.

The regeneration temperature is advantageously selected to be between 400° C. and 600° C.; it may advantageously vary during regeneration. The end of regeneration is detected when there is no more oxygen consumption—an indication that combustion of the coke is complete.

The effluent obtained from the last adiabatic reactor of step e) is optionally sent to a single phase type gas exchanger in which it is "desuperheated" without being condensed by exchange of heat with the compressed feed obtained from step d), which is itself superheated.

Said "desuperheated" effluent is then advantageously sent to a second gas/liquid type exchanger in which it is partially condensed by heat exchange in order to vaporize the vaporization feed.

Said effluent is then cooled further by heat exchange with the ethanol feed during step a) for preheating the ethanol feed.
Separation Step f)

In accordance with the invention, the effluent obtained from the last adiabatic reactor of step e) undergoes a step f) for separation into an effluent comprising ethylene at a pressure of less than 1.6 MPa, preferably less than 0.8 MPa, and an effluent comprising water.

Step f) for separation of said effluent obtained from the last adiabatic reactor of step e) may advantageously be carried out using any method known to the skilled person such as, for example, a gas/liquid separation zone, preferably a gas/liquid separation column.

The effluent comprising ethylene at a pressure of less than 1.6 MPa then advantageously undergoes a compression. Said compression allows the pressure of said effluent to be raised to a pressure which is advantageously in the range 2 to 4 MPa, which is necessary for its purification.
Purification Step g)

In accordance with the invention, the effluent comprising water obtained from the separation step f) undergoes a purification step g). The purification step g) may be carried out using any purification method which is known to the skilled person. By way of example, the purification step g) may advantageously be carried out using ion exchange resins, by adding chemical agents such as sodium hydroxide or amines, for example, to adjust the pH, and by adding chemical agents such as, for example, polymerization inhibitors selected from bisulphites and surfactants to stabilize the products.

At least one flow of treated water and at least one flow of diluting water comprising ethanol are then separated. This ethanol corresponds to ethanol which has not been converted in step e). The separation may be used to obtain a flow of ethanol-free treated water (less than 10% by weight of ethanol, preferably less than 1%), which limits the loss of ethanol, and may be carried out using any separation method known to the skilled person. By way of example, the separation may advantageously be carried out by distillation, using molecular sieves, steam or heat stripping or by solvent absorption using glycolated solvents, for example.

A flow containing the light gases and ethanol, preferably acetaldehyde and methanol, may advantageously also be separated and recycled to step f).
Recycling and Vaporization Step h)

According to the invention, the flow of diluting water comprising the ethanol obtained from purification step g) undergoes a step h) for recycling and vaporization.

At least a portion of the flow of diluting water comprising ethanol obtained from step g) undergoes vaporization using heat exchange with a quench flow obtained from the oxidation step j) in a vaporization exchanger. The term "at least a portion" means a quantity which is carefully selected so that at least 50%, preferably 80% is vaporized at the outlet from the vaporization exchanger. The quench flow obtained from step j) is partially, preferably completely, condensed during said heat exchange then recycled to the oxidation step j).

The pressure of the step h) for recycling and vaporization of diluting water comprising ethanol is adjusted so as to allow injection without compression of the vaporized flow of diluting water comprising ethanol upstream of step e). In the case in which the flow of diluting water comprising ethanol is partially vaporized by heat exchange with the quench flow obtained from step j), the non-vaporized portion is separated, decompressed, and recycled to the inlet to step c).

In a preferred arrangement, the flow of diluting water comprising ethanol obtained from step h) is injected into the inlet to step e).

In another preferred arrangement, the flow of diluting water comprising ethanol obtained from step h) is injected into the inlet to a single phase gas/gas exchanger in step d) for compression and superheating.

The non-vaporized portion of the flow of diluting water comprising ethanol obtained from the purification step g) comprising the non-vaporized fraction following heat exchange, as well as the portion which has not undergone heat exchange, is advantageously recycled and mixed with the pre-treated ethanol feed at the inlet to the vaporization step c).

By vaporizing a portion of the flow of diluting water comprising ethanol obtained from step g) and by recycling this vaporized portion upstream of step e), dilution of ethanol at the inlet to step c) is minimized. Minimizing the dilution in this manner has the effect of reducing the temperature and enthalpy of vaporization of the mixture in step c) compared with the situation in which all of the flow of diluting water comprising ethanol is recycled to the inlet of step c), meaning that evaporation of said mixture is facilitated and the energy requirements in step c) are minimized.

The flows of recycled water act as a thermal reaction diluent.

Careful adjustment of the operating conditions for the ethylene oxidation step j) and the dehydration step e) means that, by carrying out step h), the energy necessary for compression in step d) can be limited by avoiding compressing, in the vapour phase, the whole of the flow of diluting water comprising ethanol obtained from step g) by maximizing the thermal integration of the process, while reducing the total consumption of water.
Compression Step i)

In accordance with the invention, the flow comprising ethylene obtained from step f) then undergoes a compression using means known to the skilled person, for example a centrifugal or volumetric compressor, optionally multi-stage with intermediate cooling. The condensates may advantageously be mixed with the supply for the purification step g). This compression means that the effluent can be brought to a sufficient pressure to allow any purification steps which follow to take place, the operating pressure of which is directly dependent on this compressor, ignoring the pressure drops. Preferably, the discharge pressure is sufficiently high to allow direct injection of ethylene into the oxidation step j). This discharge pressure is in the range 1.1 to 5.1 MPa, preferably in the range 1.6 to 3.6 MPa.

The compressed flow then advantageously undergoes purification using means known to the skilled person, for example by one or more distillations, optionally cryogenic, and/or using resin type capture masses. Purification of the flow comprising ethylene depends on its destination, for example on the technology selected for oxidation step i), or on the possibility or otherwise of producing ethylene without oxidizing it (at the same time as the production of ethylene oxide).

Oxidation Step j)

In accordance with the invention, at least a portion of the flow comprising ethylene obtained from separation step f), compressed in compression step i) and optionally purified, is directed to an oxidation step j). This oxidation step comprises a set of equipment, catalysts and chemical products which are known to the skilled person to allow the oxidation of ethylene to form ethylene oxide.

The oxidation catalyst is advantageously based on silver. The reaction selectivity may advantageously be optimized by controlling the temperature of the reaction, and optionally by using methane dilution. This methane may derive either from storage or from a methane production unit.

An adjustment of these parameters means that the quantity of heat released by the reaction can be controlled, and as a consequence the heat extracted via evaporation of the quench fluid and the heat recoverable by condensation of this fluid in step h) can be controlled.

In accordance with the invention, the temperature of the ethylene oxidation reaction is controlled at between 100° C. and 500° C., preferably in the range 150° C. to 300° C., by means of vaporization of a heat transfer flow, termed the quench flow, in the shell of one or more multitube reactor(s), the reaction taking place in the tubes. The quench flow preferably comprises water and may advantageously be a process water flow, distilled water flow or any other flow comprising water which is not or is only slightly fouling. The temperature of the reaction may, for example, be controlled by varying the pressure on the shell side of the reactor or reactors, which has the effect of varying the vaporization temperature of the quench fluid.

The vaporization pressure of the quench flow, and thus its vaporization temperature, is selected so as to maximize the density of the flow of heat in the exchanger or exchangers of step h) for recycling and vaporization of diluting water comprising ethanol. The approach to thermal equilibrium of an exchange of heat is defined as the minimum absolute value for the temperature difference between the two sides of the exchange of heat under consideration. The vaporization pressure of the quench flow is selected in a manner such that the approach to thermal equilibrium in the exchangers of step h) is a maximum, preferably more than 10° C., preferably more than 30° C. This means that the exchange surface and the cost of the vaporization exchanger(s) of step h) can be minimized.

The oxidation step j) produces at least one effluent comprising ethylene oxide and at least one quench flow which is partially or completely vaporized which is then directed to the step h) for recycling and vaporization.

DESCRIPTION OF THE FIGURES

FIG. 1 is a diagrammatic representation of the process for the dehydration of ethanol followed by oxidation of the ethylene produced in the case of a concentrated feed of ethanol with a recycle of a flow of diluting water comprising ethanol obtained from step h) of the process.

The ethanol feed 1 is preheated in an exchanger a) with the effluent from the dehydration step e) which penetrates into the exchanger via the conduit 7. The preheated ethanol feed is then introduced into a pre-treatment zone b) via the conduit 2. The pre-treated ethanol feed is then mixed in the conduit 3 with the non-vaporized diluting water comprising ethanol obtained from the recycling and vaporization zone h) which is recycled via the conduits 23 so as to act as a reaction diluent. This mixture, constituting the vaporization feed, is introduced via line 3 into the vaporization step c) in which said mixture undergoes heat exchange with the effluent obtained from the dehydration step e) which penetrates into the exchanger via the conduit 23 in a manner such as to produce a vaporized feed. The latent heat, also known as the enthalpy of condensation, of the effluent obtained from the dehydration step e) is used to vaporize the vaporization feed without adding external heat.

The vaporized feed is then sent to the compression and superheating step d) via the conduit 4. In the compression and superheating step d), said vaporized feed is compressed and superheated and the effluent obtained from the dehydration section e), in the gaseous state, is "desuperheated" without being condensed.

Said vaporized, compressed and superheated feed is then mixed with the vaporized flow of diluting water comprising ethanol obtained from recycling and vaporization step h) then introduced into step e) in which it passes through a furnace or other equipment known to the skilled person so as to bring it to a temperature which is compatible with the dehydration reaction temperature.

The effluent obtained from the dehydration section e) then undergoes three successive exchanges described above in steps d), c) and a).

The effluent obtained from step a) is sent via the conduit 8 to the separation section f) where it is separated into an effluent 9 comprising ethylene and an effluent 14 comprising water.

The effluent comprising ethylene is sent to the compression step i) via the line 9. Step i) can be used to bring said effluent comprising ethylene to a pressure sufficient for it to be purified, and preferably a pressure which is compatible with the supply pressure for the oxidation section j). Step i) can also be used to purify the effluent comprising ethylene by separating at least one flow 17 comprising the light gases and a flow 18 of water and unreacted ethanol recycled to the purification step g).

The compressed and purified effluent 10 comprising ethylene obtained from step i) is sent to the oxidation section j) where it undergoes a conversion into ethylene oxide. Step j) can be used to form a flow 11 comprising ethylene oxide. The heat of reaction of step j) can be used to vaporize the quench fluid 13 which is then recycled via the conduit 12 to the recycling and vaporization step h).

The effluent comprising water obtained from step f) is sent to a purification step g) via the conduit 14. At least one flow of diluting water comprising unconverted ethanol and at least one flow 19 of treated water are separated. A flow 21 containing the light gases and unconverted ethanol is also separated and recycled to step f).

The whole of said flow of diluting water comprising unconverted ethanol obtained from the purification step g) is sent to the recycling and vaporization step h), where it is divided into two flows 15 and 23. The flow 15 is optionally pumped at a pressure which is compatible with injection of the flow 16 upstream of step e), then is partially or completely vaporized by means of an exchange of heat using the condensation of the vaporized quench fluid 12 obtained from the oxidation step j). The condensed quench fluid is recycled to the oxidation section j) via the conduit 13. The vaporized effluent 16 from step h) is incorporated with the pre-treated ethanol feed upstream of the dehydration step e).

The non-vaporized portion 23 obtained from step h) is recycled upstream of the vaporization step c). In the case in which vaporization of the flow 15 is not complete, the liquid portion may advantageously be decompressed and mixed with flow 23.

The following examples illustrate the invention without limiting its scope.

EXAMPLES

Example 1

In Accordance with the Invention

Example 1 illustrates a process in accordance with the invention.

The ethanol feed under consideration was produced by fermentation of wheat without extracting the gluten, employing a dry milling process.

Step a)

Said ethanol feed was introduced into an exchanger E1 at a flow rate of 45 664 kg/h at a pressure of 1.15 MPa and was heated, remaining in the liquid phase, to a temperature of 120° C. against the effluent obtained from the adiabatic reactor of step e).

Step b)

The heated ethanol feed was pre-treated over a TA801 resin in order to eliminate traces of nitrogen-containing compounds. During this pre-treatment, a portion of the ethanol was converted into DEE. The characteristics of the unrefined and pre-treated ethanol feed are given in Table 1.

TABLE 1

Characteristics of ethanol feed before and after pre-treatment (percentages by weight)

|  | ETHANOL FEED | ETHANOL AFTER PRETREATMENT |
|---|---|---|
| ETHANOL | 91.2% | 82.1% |
| H2O | 8.7% | 10.5% |
| DEE | 0% | 7.3% |
| NITROGEN-CONTAINING COMPOUNDS | 0.005% | 0.000% |

Step c)

The vaporization feed, constituted by the pre-treated ethanol feed mixed with 85380 kg/h of diluting water and unconverted ethanol recycled in accordance with step h), was introduced into an exchanger E2 at a pressure of 0.37 MPa. The vaporization feed entered the exchanger E2 at 113° C. and was thus already vaporized to an extent of 8% by weight. The pressure at the inlet to the exchanger E2 was adjusted so that the approach to thermal equilibrium with the flow obtained from the last adiabatic reactor of step e) was a minimum of 15° C.

In step c), the majority of the latent heat of the aqueous phase of the effluent obtained from the last adiabatic reactor of step e) was recovered in order to vaporize the vaporization feed without adding external heat. Thus, 51.9 MW was exchanged between said vaporization feed and said effluent.

Step d)

The vaporized feed was then compressed in an integrally geared centrifugal compressor K1 in a manner such that the pressure of said vaporized feed was equal to 0.695 MPa at the end of compression.

The compressed feed was then heated in a single phase type gas exchanger E3 using an exchange of heat with the effluent obtained from the adiabatic reactor of step e). In said single phase type gas exchanger, said compressed feed was superheated to a temperature of 419° C. and the effluent obtained, in the gaseous state, from the last adiabatic reactor of step e) was "desuperheated" without being condensed and had a temperature of 273° C.

Step e)

Dehydration step e) comprised two furnaces and two adiabatic reactors in series.

Said feed, compressed and heated in said single phase type gas exchanger, was then mixed with 55590 kg/h of vaporized diluting water obtained from the recycling and vaporization step h). This mixture was then introduced into a furnace so as to bring it to an inlet temperature for the first adiabatic reactor of step e) which was compatible with the temperature of the highly endothermic dehydration and conversion reaction of DEE to ethylene, i.e. to a temperature of 470° C. The outlet temperature from the last adiabatic reactor of step e) was 420° C.

The degree of dilution at the reactor inlet (i.e. the water/ethanol weight ratio) was 3.

Trapping the nitrogen-containing compounds in pre-treatment step b) meant that the inlet temperature to the first adiabatic reactor of step e) could be considerably reduced.

Said compressed and heated feed was introduced into the first adiabatic reactor at an inlet pressure of 0.595 MPa. The pressure of the effluent at the outlet from the last adiabatic reactor from step e) was 0.500 MPa. The dehydration step e) was operated at a weight hourly space velocity of 7 h$^{-1}$.

The adiabatic reactor contained a fixed bed of dehydration catalyst, said catalyst comprising 80% by weight of ZSM-5 zeolite treated with $H_3PO_4$ such that the phosphorus P content was 3% by weight.

The conversion of the ethanol feed in step e) was 95%.

Step f)

The effluent obtained from the last adiabatic reactor of step e) then underwent three exchanges of heat as described above and was sent to a gas/liquid separation column. An effluent comprising ethylene at a pressure of 0.36 MPa was then separated, along with an effluent comprising water. This separation was carried out using a gas/liquid separation column with a recycle of the water produced at the column bottom to the head of the column and after cooling and injecting a neutralizing agent.

Step g)

A flow of diluting water comprising unconverted ethanol 15 as well as a flow containing light gases 21 was then separated by conventional low pressure distillation of the impure water. A flow of treated water was separated 19 and constituted the purge for the process; its partial water flow rate corresponded to the water formed by the dehydration reaction of step e).

Step h)

The flow of diluting water comprising unconverted ethanol was divided into two flows, 23 and 15. The flow 15 was sent to a reboiler in order to vaporize it using the heat supplied by the flow 12 obtained from the oxidation section j). 35 MW were exchanged in this step and could be used to vaporize 100% by weight of the flow 15. The hot flow obtained from step j) was condensed and recycled to the reactor for the oxidation step j). This flow was solely constituted by 65914 kg/h of distilled water; its inlet pressure into step h) was 1.5 MPa at its dew point temperature, in this case 200° C.

The vaporized flow 16 was recycled upstream of the step e) and the liquid flow 23 was recycled upstream of step c).

Step i)

The effluent comprising ethylene then underwent compression to raise its pressure to 2.78 MPa before its final purification carried out with cryogenic distillation. A flow 17 of light gases was separated from the head of this column and a flow of condensates comprising water and ethanol was recycled to step g).

Step j)

The purified ethylene effluent obtained from step i) was sent to the oxidation section j). The operating conditions for this section were as follows:

conversion per pass: 16%;
selectivity: 85% molar for ethylene;
$O_2$/ethylene ratio=7;
supply pressure to oxidation reactor: 20 barg;
reactor inlet temperature: 230° C.;
exothermicity of reaction: 40° C.

The exothermicity of the reaction, and thus its selectivity, was limited because of a large dilution of the reaction medium by methane which was recycled to the process. The methane was purified using an absorption column employing a solution of potassium carbonate.

The reactor was a multitube reactor for generating 65914 kg/h of saturated vapour at a pressure of 1.5 MPa. This vapour was sent to the recycling and vaporization section h) by means of the flow 12.

The ethylene oxide was separated in a water absorption column followed by a stripping column.

A mixture of additional oxygen and methane was injected into the oxidation section j) via the conduit 22.

The purified ethylene oxide was extracted in the flow 11 before being sent to an ethylene glycol conversion section.

The various flows, in kg/h, are consigned to Table 2:

TABLE 2

| Composition of principal flows | | | | | | | |
|---|---|---|---|---|---|---|---|
| Current | | 1 | 2 | 3 | 4 | 5 | 6 |
| Temperature | ° C. | 25 | 120 | 113 | 132 | 419 | 420 |
| Water | kg/h | 3993 | 3993 | 88133 | 88132.6 | 88132.6 | 158602 |
| Ethanol | kg/h | 41671 | 41671 | 42903 | 42903 | 42903 | 2187 |
| DEE | kg/h | | | 8 | 8 | 8 | 14 |
| Ethylene | kg/h | | | 0 | 0 | 0 | 25228 |
| | kg/h | | | | | | |
| Other (light + oxygen-containing) | kg/h | | | | | | 603 |
| Total | | 45664 | 45664 | 131044 | 131044 | 131044 | 186634 |
| Current | | 8 | 19 | 16 | 12 | 13 | 17 |
| Temperature | ° C. | 135 | 25 | 170 | 200 | 35 | 25 |
| Water | kg/h | 158602 | 19680 | 54782 | 65914 | 65914 | |
| Ethanol | kg/h | 2187 | 103 | 802 | | | 50 |
| DEE | kg/h | 14 | | 6 | | | |
| Ethylene | kg/h | 25228 | | | | | |
| Ethylene oxide | kg/h | | | | | | |
| Other (light + oxygen-containing) | kg/h | 603 | 100 | | | | 503 |
| Total | | 186634 | 19883 | 55590 | 65914 | 65914 | 553 |
| Current | | 23 | 9 | 10 | 11 | 22 | |
| Temperature | ° C. | 143 | 35 | 25 | 35 | 35 | |
| Water | kg/h | 84140 | 300 | | | | |
| Ethanol | kg/h | 1232 | 150 | | | | |
| DEE | kg/h | 8 | 0 | | | | |
| Ethylene | kg/h | | 25228 | 25228 | | | |
| Ethylene oxide | kg/h | | | | 33438 | | |
| Other (light + oxygen-containing) | kg/h | | 503 | | | 8210 | |
| Total | | 85380 | 26181 | 25228 | 33438 | 8210 | |

The light compounds are C3 and C4 hydrocarbon compounds as well as hydrogen and carbon dioxide.

The selectivity of the process for the transformation of ethanol into ethylene was 99%.

It was calculated as follows: (ethylene contained in effluent comprising ethylene)/(0.61*quantity of converted ethanol), where the quantity of converted ethanol is the ethanol contained in the ethanol feed before pre-treatment minus the ethanol contained in the purged flows of water and in the effluent comprising ethylene. 0.61 g is the maximum quantity of ethylene obtained by dehydrating 1 g of pure ethanol.

This example shows that the exchanger E3 can be used to recover 35 MW of thermal energy obtained from the oxidation section in order to vaporize diluting water from the dehydration section. The thermal energy of this heat source was substantially higher (200° C. in this example) than the temperature for the vaporization of the diluting water comprising ethanol (approximately 135° C. in this example), and so the density of the heat flux passing through the exchanger E3 was high compared with a prior art process where vaporization of the diluting water is carried out by exchange with the effluent from the dehydration step e).

In addition, the fact of using a closed loop of distilled water to recover heat produced in the oxidation step j) has the advantage of not necessitating a purification section for the quench water before recycling it (compared with a process in which the diluting water is used directly as a quench fluid in the shell of the oxidation reactor before being injected into the dehydration section).

The fact that the whole of the flow of diluting water comprising ethanol obtained from step g) is not compressed means that the power necessary for compression in step d) can be reduced by 40% compared with a prior art process in which the flow of diluting water comprising ethanol obtained from step g) is recycled in its entirety upstream of the vaporization step c).

The invention claimed is:

1. A process for the dehydration of an ethanol feed to ethylene then oxidation of the ethylene to ethylene oxide, comprising:
    a) an optional step for preheating said ethanol feed to a temperature in the range 70° C. to 130° C. by heat exchange with the effluent obtained from step e);
    b) an optional step for pre-treatment of the ethanol feed over an acidic solid operating at a temperature in the range 70° C. to 130° C. in order to produce a pre-treated ethanol feed;
    c) a step for vaporization of a vaporization feed comprising said optionally pre-treated ethanol feed and at least a portion of the flow of diluting water comprising ethanol recycled in accordance with step h) to an exchanger by means of an exchange of heat with the effluent obtained from the last reactor of step e), said vaporization feed being introduced into said vaporization step at a pressure in the range 0.1 to 1.4 MPa so as to produce a vaporized feed;
    d) a step for compressing and superheating said vaporized feed in a compressor so as to produce a compressed feed which is at the temperature for supplying to the dehydration section e);
    e) a step for dehydration of a mixture comprising said compressed feed and the vaporized flow of diluting water comprising the ethanol obtained from step h), said mixture having a ratio of water to ethanol in the range 1 to 4 by weight, in at least one adiabatic reactor containing at least one dehydration catalyst and in which the dehydration reaction takes place, operating at an inlet temperature in the range 350° C. to 550° C. and at an inlet pressure in the range 0.3 to 1.8 MPa;
    f) a step for separating the effluent obtained from the last adiabatic reactor of step e) into an effluent comprising ethylene at a pressure of less than 1.6 MPa and an effluent comprising water;
    g) a step for purification of at least a portion of the effluent comprising water obtained from step f) and separation into at least a flow of treated water and a flow of diluting water comprising ethanol;
    h) a step for recycling and vaporization of at least a portion of the flow of diluting water comprising ethanol obtained from step g) by partial or total vaporization in an exchanger using heat exchange with a quench flow obtained from oxidation step j) in a vaporization exchanger, said quench flow being cooled and then being recycled to the reactor or reactors of oxidation step j), said flow of at least partially vaporized diluting water comprising ethanol being recycled upstream of step e), the non-vaporized portion of the flow of treated water obtained from step g) being recycled to the inlet to vaporization step c);
    i) a step for compression of the effluent comprising ethylene obtained from step f);
    j) a step for oxidation of the ethylene comprised in the effluent comprising ethylene obtained from step i) into ethylene oxide, this oxidation step comprising at least one tubular oxidation reactor cooled by vaporization of said quench flow obtained from step h), said quench flow which has thus been reheated being recycled to step h).

2. The process according to claim 1, in which the flow of diluting water comprising ethanol obtained from step h) is injected into the inlet to step e).

3. The process according to claim 1, in which the flow of diluting water comprising ethanol obtained from step h) is injected into the inlet of a single phase gas/gas exchanger used in the compression and superheating step d).

4. The process according to claim 1, in which said compressed feed is heated in a single phase type gas exchanger by means of an exchange of heat with the effluent obtained from the last adiabatic reactor of step e).

5. The process according to claim 1, in which the compressed flow obtained from said step i) undergoes a purification.

6. The process according to claim 1, in which the portion of the flow of diluting water comprising ethanol obtained from step g) is exchanging heat with the quench flow in step h) such that at least 50% of said flow of diluting water is vaporized at the outlet from said vaporization exchanger.

7. The process according to claim 1, in which the pressure of the compressed feed is in the range 0.3 to 1.8 MPa.

8. The process according to claim 1, in which the effluent obtained from the last adiabatic reactor of step e) is at a temperature in the range 270° C. to 450° C., and at a pressure in the range 0.2 to 1.6 MPa.

9. The process according to claim 1, in which the dehydration step e) is carried out in one or two reactors.

10. The process according to claim 1, in which said dehydration catalyst used in step e) is an amorphous acid catalyst or a zeolitic acid catalyst.

11. The process according to claim 1, in which said ethanol feed comprises a percentage by weight of ethanol in the range 35% to 99.9% by weight.

12. The process according to claim 1, in which the optional step b) for pre-treatment is conducted and supplemented by a pre-treatment using an anion exchange resin.

13. The process according to claim 1, wherein the optional steps a) and b) are both conducted.

* * * * *